US008256286B2

(12) United States Patent
Carroll et al.

(10) Patent No.: US 8,256,286 B2
(45) Date of Patent: Sep. 4, 2012

(54) SYSTEM AND METHOD FOR DETECTING AND MEASURING ETHYL ALCOHOL IN THE BLOOD OF A MOTORIZED VEHICLE DRIVER TRANSDERMALLY AND NON-INVASIVELY IN THE PRESENCE OF INTERFERENTS

(75) Inventors: John Carroll, West Palm Beach, FL (US); Catherine Carroll, West Palm Beach, FL (US); Dennis Bellehumeur, Fort Lauderdale, FL (US)

(73) Assignee: Sober Steering Sensors, LLC, Boca Raton, FL (US)

( * ) Notice: Subject to any disclaimer, the term of this patent is extended or adjusted under 35 U.S.C. 154(b) by 89 days.

(21) Appl. No.: 12/766,662

(22) Filed: Apr. 23, 2010

(65) Prior Publication Data

US 2010/0269566 A1    Oct. 28, 2010

Related U.S. Application Data

(60) Provisional application No. 61/172,383, filed on Apr. 24, 2009.

(51) Int. Cl.
*G01N 19/00* (2006.01)
(52) U.S. Cl. ................... 73/335.04
(58) Field of Classification Search .......... 73/23.3, 73/23.34, 335.04, 31.01, 31.02, 31.03, 31.05; 600/306
See application file for complete search history.

(56) References Cited

U.S. PATENT DOCUMENTS

| 4,613,845 | A | | 9/1986 | Du Bois |
| 5,793,292 | A | | 8/1998 | Ivey, Jr. |
| 5,928,609 | A | * | 7/1999 | Gibson et al. .......... 422/90 |
| 5,944,661 | A | * | 8/1999 | Swette et al. ........ 600/345 |
| 5,969,615 | A | | 10/1999 | Ivey, Jr. et al. |
| 6,075,444 | A | | 6/2000 | Sohège et al. |
| 6,620,108 | B2 | * | 9/2003 | Duval et al. .......... 600/532 |
| 7,076,371 | B2 | * | 7/2006 | Fu .......... 702/19 |
| 7,611,461 | B2 | | 11/2009 | Hawthorne et al. |
| 2004/0236199 | A1 | | 11/2004 | Hawthorne et al. |
| 2005/0087382 | A1 | | 4/2005 | Bellehumeur |
| 2005/0230175 | A1 | * | 10/2005 | Brown et al. ........ 180/272 |
| 2006/0016244 | A1 | * | 1/2006 | Duval .......... 73/23.3 |
| 2006/0237252 | A1 | | 10/2006 | Mobley et al. |
| 2006/0237253 | A1 | | 10/2006 | Mobley et al. |
| 2006/0237310 | A1 | | 10/2006 | Patel et al. |
| 2008/0009693 | A1 | | 1/2008 | Hawthorne et al. |
| 2009/0087920 | A1 | * | 4/2009 | Pettersson et al. .......... 436/132 |

* cited by examiner

OTHER PUBLICATIONS

International Search Report. PCT/US2010/032359, dated Jun. 14, 2010; Cover page of WO 2010/124275 A1.

*Primary Examiner* — Hezron E Williams
*Assistant Examiner* — Jamar Ray
(74) *Attorney, Agent, or Firm* — Howard M. Gitten; Edwards Wildman Palmer LLP (57) ABSTRACT

This invention relates to a system and method that can quickly and accurately detect and measure ethyl alcohol in the blood of a motorized vehicle driver transdermally and non-invasively within minutes of ethanol consumption and in the presence of interferents. The system includes an array of sensors embedded into the steering mechanism of a motorized vehicle, a data base of patterns produced through empirical testing of various analytes in various combinations and concentrations, neural net based pattern recognition algorithms to ascertain the driver's transdermal alcohol concentration and a database derived from human testing, correlating the driver's transdermal alcohol concentration with the driver's blood alcohol concentration. The detection system is integrated with a motor vehicle decision module which can prevent the operation of a motorized vehicle by a driver whose BAC exceeds a preset limit.

13 Claims, 5 Drawing Sheets

SYSTEM AND METHOD FOR DETECTING AND MEASURING ETHYL ALCOHOL IN THE BLOOD OF A MOTORIZED VEHICLE DRIVER TRANSDERMALLY AND NON-INVASIVELY IN THE PRESENCE OF INTERFERENTS

CROSS-REFERENCE TO RELATED APPLICATION

This application claims priority to U.S. Provisional Application No. 61/172,383 filed on Apr. 24, 2009 in its entirety.

BACKGROUND OF THE INVENTION

This invention relates to a system and method that can quickly and accurately determine the presence of ethyl alcohol (ethanol) in the blood of a driver of a motorized vehicle and accurately measure the concentration of the ethanol transdermally and non-invasively within minutes of ethanol consumption and in the presence of interferents. The system, which uses an array of sensors embedded into the steering mechanism of a motorized vehicle, a pattern recognition library, and associated pattern recognition, analyte identification and interferent discrimination algorithms, to ascertain the presence of ethanol in a driver's blood by measuring a driver's transdermal alcohol concentration. If the measured ethanol exceeds a preset limit, interlock systems are activated which prevent movement of the vehicle.

Driving under the influence of alcohol has been and continues to be the number one cause in fatal automobile accidents in the United States. While progress has been made over the last few decades in preventing drunk drivers (or alcohol impaired drivers) from operating automobiles, the problem persists and accidents involving drunk drivers kill on average 36 people and injure 700 people everyday. However, with the right technology, most if not all of these deaths and injuries caused by drunk drivers could be prevented.

Breathalyzer systems are the primary means currently available to combat alcohol impaired driving. However, as breathalyzer systems are typically conspicuous, cumbersome and very intrusive to a driver, breathalyzer systems have very low compliance rates from the driving under the influence ("DUI") offenders who have received a mandate to use them. What is needed is an in-vehicle alcohol detection system that is non-intrusive to the extent that its utilization is seamless with the driving task.

Many other systems have been devised to attempt to gauge the impairment of a driver before or during the driver's operation of a vehicle and combat drunk driving. Some systems have attempted to directly measure a driver's impairment by requiring the driver to push buttons in a random order within a given amount of time. Other systems have attempted to determine the driver's blood alcohol concentration by measuring tissue alcohol concentration or breathe alcohol concentration. However, the complexity, expense and intrusiveness of these systems typically make them impractical for widespread usage and compliance. In addition, the accuracy of many devices in the prior art is greatly reduced when various interferents (substances other than ethanol) are present. These interferents such as butane, gasoline, perfume or alcohol based products may mark or confuse prior art sensors to indicate a false positive or fail to indicate a masked ethanol presence. What is needed is a system that provides a quick and accurate determination of ethanol in a driver's blood, provides the determination non-invasively and in the presence of any interferents, and is practical for widespread use.

BRIEF SUMMARY OF THE INVENTION

An in-vehicle alcohol detection system and method for using a combination of sensors embedded in the steering mechanism of any motorized vehicle to detect the presence of ethanol in a driver's blood and determine the concentration of ethanol in a driver's blood transdermally, quickly, accurately, and non-invasively within minutes of initial ethanol consumption by the driver and in the presence of interferents. The in-vehicle alcohol detection system is compact enough for its components to fit inside the steering mechanism of a motor vehicle and is a component in a drunk driving prevention system that can be incorporated into a motorized-vehicle which can prevent the operation of the vehicle by a driver who has ingested any alcohol or whose blood alcohol concentration ("BAC") exceeds a preset limit.

The presence of ethanol in a driver's blood is detected through the measurement of the driver's transdermal alcohol concentration ('TAC'). A driver's TAC is measured by collecting the pre-perspiratory vapor emanating from the driver's hands, subjecting an array of sensors to the vapor, then using a pattern recognition library together with associated pattern recognition, analyte identification and interferent discrimination algorithms, to process the sensor response data. If a TAC greater than 0 is measured, ethanol is known to be present in the driver's blood and appropriate interlocks are activated in a zero tolerance situation. Actual blood alcohol concentration ('BAC') levels can also be determined, by the in-vehicle alcohol detection system, by first measuring the driver's TAC and then using a look-up table database derived from intravenous human testing, to find the BAC which corresponds to the driver's TAC. The database may include physiological and metabolic information specific to the driver.

Significantly, the present invention can make an accurate TAC measurement even in the presence of interferents. This is due to the unique combination of one or more chemicapacitive sensor arrays, and the pattern recognition, analyte identification and interferent discrimination algorithms, which provide both identification and quantification of analytes present.

In one embodiment, chemicapacitive sensors within each sensor array are coated with selectively absorbing materials, such as chemi-absorbent polymers, as a dielectric. The ethanol and interferents (analytes) are absorbed into the dielectric, changing its permittivity, and leading to an increase or decrease in capacitance of the sensor. Changes in capacitance can be electrically detected and measured.

The sensors are designed so that at least two sensors respond differently to the same analyte. Therefore, in one embodiment, polymers are chosen which absorb specific target analytes. Each sensor has a specific and different polymer coating, based on the polymer's ability to absorb target analytes. Each polymer coating reacts in a distinct way to each analyte. When detected by a sensor, different ethanol concentrations or ethanol/interferent mixtures will create a distinct capacitance change resulting in a distinct sensor response. Consequently, different ethanol concentrations or chemical mixtures will create specific and unique discernable patterns of sensor response spikes that are observable by simultaneously viewing the individual sensor responses across the sensor array.

The resulting response pattern is then processed through a pattern recognition library, which contains a multitude of patterned responses corresponding to sensor outputs for ethanol and of potential interferents for each distinct polymer. The response to each analyte is measured and recorded at multiple concentrations, temperatures, and humidity levels for each distinct polymer and stored in the pattern recognition library. A processor makes use of pattern recognition, analyte identification and interferent discrimination algorithms to classify, i.e. identify and quantify the analytes in the vapor.

In the chemicapacitive sensor array, different polymers are used in each sensor to provide a basis for interferent rejection in addition to adding greater redundancy and precision. The chemicapacitive sensor array can also be used in combination with other sensor technologies, such as chemi-resistive, metal oxide and electrochemical sensors for increased sensitivity and interferent identification.

The output from each sensor-polymer combination is fed through a channel in the pattern recognition library specific to that polymer. This occurs simultaneously, in separate channels, for each sensor-polymer combination. The sensor responses from each polymer channel are then processed in accordance with pattern recognition algorithms to identify the possible combinations of analytes producing such a signal from a given sensor-polymer combination. The analyte identification and discrimination algorithms are then used to determine the identity and concentration of each analyte present. In the case of a 'zero tolerance' system, merely identifying the presence of ethanol is sufficient. For a calculation of BAC, The algorithms utilize the output from the pattern recognition library to identify and quantify the analytes detected by the sensors, These algorithms, which may include linear regression modeling, artificial neural networks and/or statistical analysis, are then used to interpret the pattern recognition library output, identifying and quantifying analytes present. Once identified and quantified, the sensor responses attributed to interferents are subtracted from the overall sensor array response. This results in an accurate TAC measurement, which can then be correlated to the driver's corresponding BAC using an imbedded human testing database which may include physiological data from the driver.

It is an object of the invention to provide a system that is practical for widespread use and can provide a quick, accurate, and non invasive determination of whether there is alcohol present in a driver's blood in the presence of any interferents. It is another object of the invention to provide a system that is practical for widespread use and can provide a quick, accurate, and non invasive determination of a driver's actual BAC level in the presence of interferents.

DETAILED DESCRIPTION OF THE PREFERRED EMBODIMENTS

An in-vehicle alcohol detection system and method that uses the combination of a chemicapacitive sensor array, a pattern recognition library, and associated pattern recognition, analyte identification and interferent discrimination algorithms, to transdermally detect the presence of ethanol in a driver's blood, quickly, accurately, and non-invasively within minutes of initial ethanol consumption by the driver, and in the presence of interferents. The system then indicates to a Vehicle Decision Module the presence or absence of ethanol in the driver's blood, allowing the Vehicle Decision Module to make a decision on whether to allow or prevent the driver from operating the motorized vehicle.

Generally, the sensor array(s) used by the in-vehicle alcohol detection system are comprised of multiple sensors. At least two individual sensors within the array respond to an identical analyte in a different way. In one embodiment of the invention, the sensors are chemicapacitive sensors, and each has its own unique polymer coating. The sensors are based on micro-electro-mechanical systems (MEMS) devices using changes in capacitance as the measurand.

Figure 1:
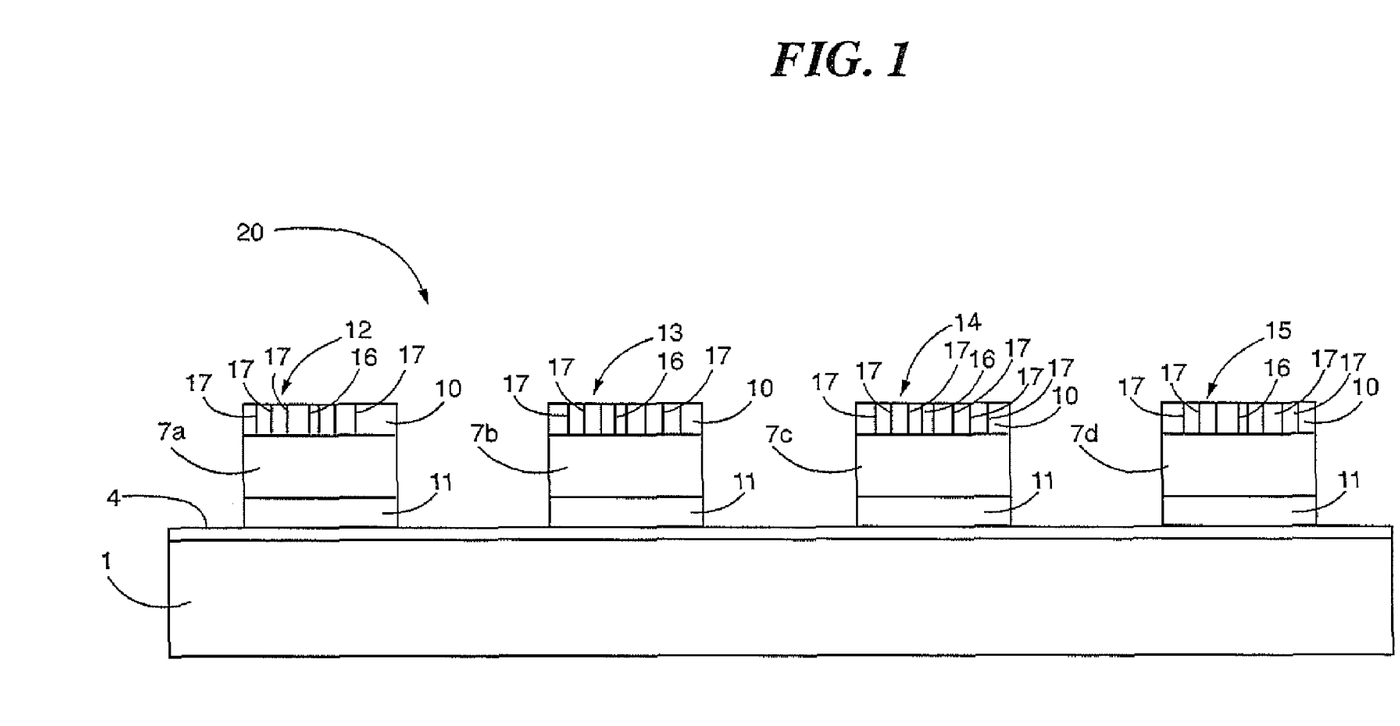
FIG. 1 is a schematic drawing of a sensor array which operates in accordance with the invention.

More specifically, the sensor array is made up of a plurality of electro-pairs as shown in FIG. 1. Each member of the pair is a drive electrode or a sense electrode. Generally, a sensor array 20 includes a substrate 1. A shield layer 4, in one non-limiting example, is disposed on a surface of substrate 1. Different polymer sensing materials 7a-7d are used to coat the various electrode pairs. Each electrode pair having a distinct and separate polymer.

Sensing electrode pairs 12, 13, 14 and 15, each contain a respective drive 10 and sense 11 electrode elevated above the surface of the substrate 1. Respective bore 16 provides a passage for filling the polymer 7a-7d into the sensor polymer 7a-7d. Vents 17 allow for vapor to enter and leave the respective sensor.

These microcapacitive transducers are microelectromechanical systems (MEMS) devices. They can be either in the form of a fixed parallel plate disk, typically 350 um in diameter, or elevated interdigitated sensor elements approximately 400 um×500 um having alternating sense 11 and drive electrode 10 of electrode pairs 12, 13, 14 and 15 (each beam typically separated by 3.5 um), in parallel, supported by 2 um tall insulating posts above the lower substrate 1. The interaction between a target analyte and polymer 7 modifies the dielectric properties of the polymer, resulting in a change in capacitance of the sensor in the pF range. The MEMS device may include analog amplification, an analog-to-digital converter, and digital intelligence for calibration, linearization, and temperature and humidity compensation.

The amount of analyte that is absorbed by a polymer depends on the polymer's chemical properties. By way of example, non-polar polymers tend to absorb non-polar analytes. Conversely, polar polymers tend to absorb polar analytes. Consequently the different polymer coatings of the sensors are selected for detection of the analyte ethanol in the presence of anticipated interferents. The sensor response spike is measured from a baseline, so that the higher the chemical concentration, the larger the observable response; such as change in voltage over time resulting from the change in capacitance.

Sensor array 20 may also include sensors for ambient humidity and temperature. These sensors may be MEMS fabricated integrally with substrate 1. However, it is also possible to form the sensors as discrete elements.

The plurality of sensors (electrode pairs 12-15) within each sensor array 20 is crucial for proper interferent rejection. Typically, prior art real time ethanol field detectors are prone to false readings when interfering chemicals are present. Individually, any one sensor 12, 13 14 or 15 may be unable to distinguish between ethanol and interferent, but when multiple sensors are used in combination, individual analytes can be identified and quantified. By comparing the responses of multiple chemicapacitors, each coated with a different polymer, it becomes possible to distinguish interferents from ethanol by using the resulting polymer response patterns.

To reliably measure TAC, the in-vehicle alcohol detection system takes the output of the sensor array 20, identifies and quantifies all analytes detected, then subtracts the interferents' contribution to the overall sensor responses, leaving only the contribution of the ethanol; if any.

A sensor array 20 may be composed of ten sensors, by way of non-limiting example (each may be constructed in accordance with FIG. 1 discussed above), with each sensor coated with a different polymer 7 to maximize coverage over chemical space. Each sensor produces a respective output signal having a peak of varying height when presented with an analyte. The peak height is proportional to the concentration of the analyte, which, in turn, is a function of the polymer with which a sensor is coated. In the best case scenario, at least one sensor will provide a unique signal peak for each analyte, and, at least two sensors produce different signals in the presence of an identical analyte. This pattern of sensor responses resulting from the individual changes generated by each sensor across the sensor array 20 allows for detection, identification, and measurement of ethanol or any other target analyte, even in the presence of a wide spectrum of possible interferents. Further, detection and system utility are maximized by identifying polymers that have a uniqueness of response to targeted analytes (e.g. ethanol) from likely possible interferents.

The second component of the in-vehicle alcohol detection system is the use of a pattern recognition library, and associated pattern recognition, analyte identification and interferent discrimination algorithms, to identify and measure ethanol in the presence of interferents. The CPU utilizing data stored in the pattern recognition library, through the use of pattern recognition algorithms, identifies and quantifies analytes that are detected by the sensors. The library contains response patterns representing different mixtures and concentrations of ethanol and interferents for each polymer. Analysis techniques (discussed below), which may include artificial neural networks and statistical analysis, are then used to extract a value for TAC from an analysis of each individual signal. The actual TAC is determined by identifying and quantifying the analytes present then subtracting the interferent portion of the response from the overall response. This results in a TAC level value for each sensor-polymer combination. A probabilistic determination can then be made either of: (A) the presence or absence of ethanol; or (B) the actual vale of ethanol present.

In a preferred embodiment, the artificial neural network is used because of its ability to learn an input-output mapping over a set of examples. In this case, outputs of the pattern recognition library are used as inputs by the artificial neural network and a TAC is produced as an output of the network. In a preferred non-limiting example, inputs from the temperature and humidity sensors may also be included to compensate for the affect of the ambient environment on the sensors. Given a network architecture and a training set of input patterns (i.e. the pattern recognition library), a collection of variable weights determines the output of the network as a function of each polymer response pattern. The network architecture comprises such factors as the type of network, the number of nodes in each layer, and the connections between the nodes.

The initial neural network may be developed by: 1) starting with an initial set (populations) of solutions, where a solution is a candidate strategy for achieving some goal, 2) randomly altering (e.g. mutate and/or recombine) some or all of the individuals of the current data population, 3) evaluate the worth of each individual of the population in light of the specified goals in quantitative terms, 4) use a selection rule to choose a subset of individual solutions in the population to be parents for the next generation, and 5) return to step 2 unless a halting criterion has been met.

Figure 3:
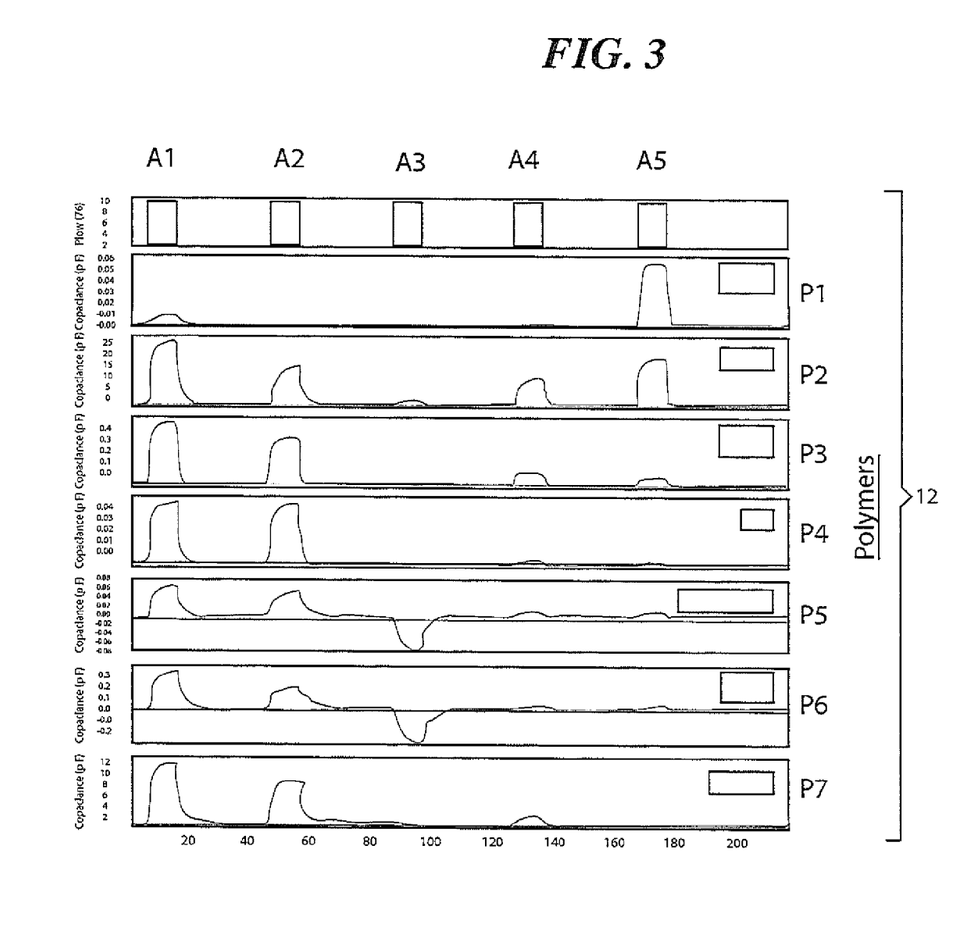
FIG. 3 is a graph representing a pattern of sensor response spikes.

Reference is now made to FIG. 3, in which a graph of sensor response spikes 19 represented as a voltage signal over time, resulting from the interaction of a respective sensor array 20 to various analytes is shown. Each sensor shown as P1-P7 representing the different polymer coatings within a sensor array 20 exhibits a distinct response to a specific analyte A1-A5 as shown. Each sensor $P_1$-$P_7$ detects the presence or absence of specific analytes in the environment surrounding the sensors. The polymers are specifically chosen to identify targeted analytes. Each polymer produces a unique type of signal peak pattern when exposed to different concentrations of specific analytes, including no peak at all. Usually, the greater the concentration of a specific analyte, the higher the peak. The uniqueness of response enables the creation of a pattern matching library. The unique pattern response of each sensor-polymer set to each analyte also enables computing device 160, utilizing the pattern recognition library and associated neural net based identification and quantification algorithms 116, to resolve this array of sensor responses 19 into a decision regarding the presence or absence of ethanol.

Figure 2:
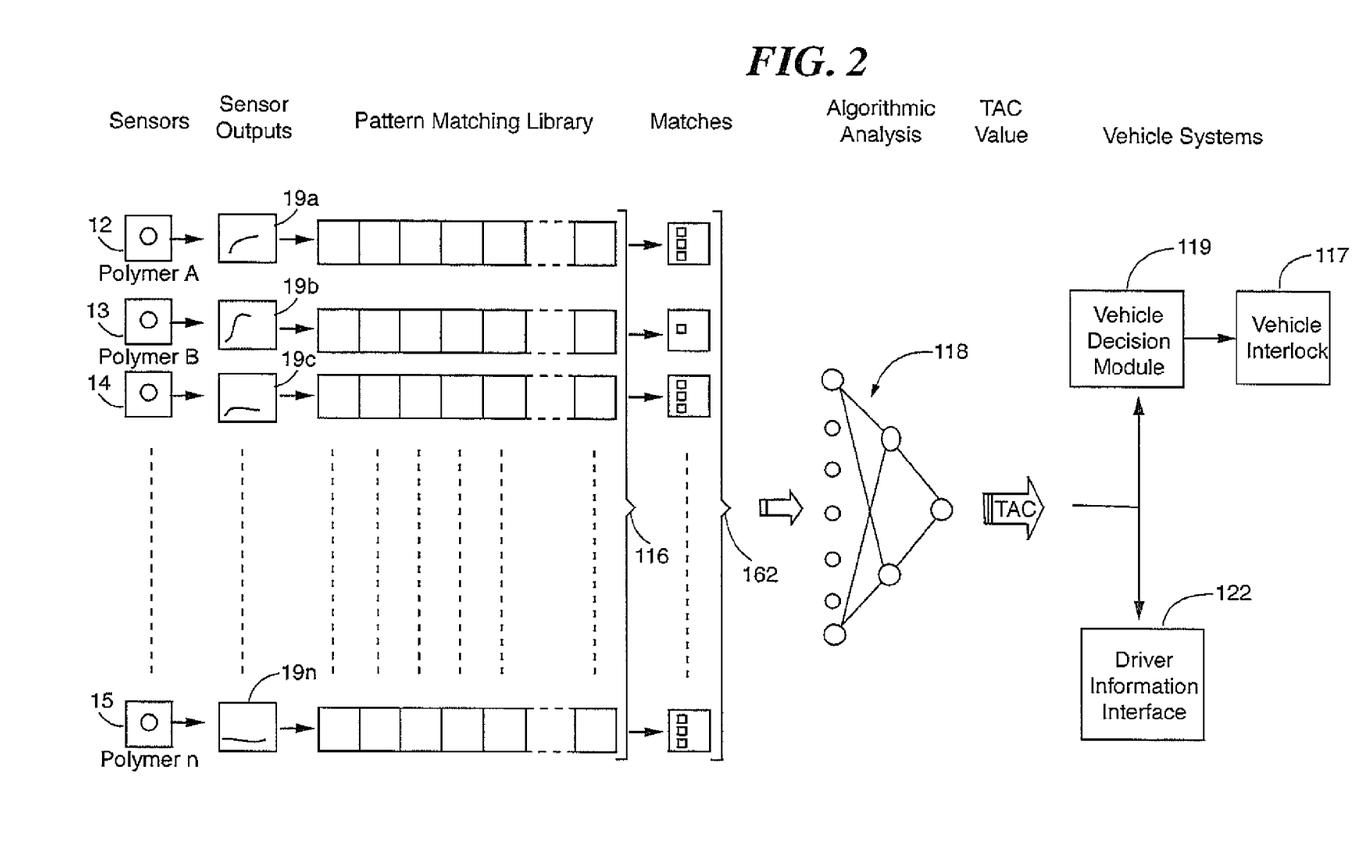
FIG. 2 is an operational flow diagram showing the process of determining the transdermal alcohol concentration of a driver of a motorized vehicle and transmitting the transdermal alcohol concentration to systems within the motorized vehicle.

Referring now to the drawings and, in particular, FIG. 2, an operational flow chart detailing the operation of the in-vehicle alcohol detection system is shown. When exposed to pre-perspiratory vapor, each sensor 12-15, within a sensor array 20, produces a unique sensor response spike 19a-19n. Taken together, these sensor response spikes 19a-19n form a sensor array response pattern that provides input to the pattern recognition library 116 and its associated pattern recognition, analyte identification and interferent discrimination algorithms, 118. As discussed above, pattern recognition library 116 includes a plurality of patterns, empirically derived through controlled test programs, corresponding to potential response patterns 19. An ASIC or CPU 160 processes the outputs from the pattern recognition library 116 using the identification and quantification algorithms, determine a TAC level. As will be shown below, the CPU and pattern recognition library 116 make up part of computing device 160. CPU 160 compares each sensor output on a channel by channel basis with known responses stored in pattern matching library 116 to produce one or more matches 162 on a per channel basis. A pattern of match results 162 is then processed by CPU 116 in accordance with algorithms, in one nonlimiting embodiment represented as neural network 118, to determine a probability that ethanol is present and/or an amount of ethanol present as a function of matches 162, which in turn is a function of the comparisons of sensor array outputs 19.

In other words, the output from the pattern recognition library 116 is then used by computing device 160 to identify and quantify the analytes, including ethanol, detected by the sensors. This results in a TAC level value.

The TAC measured value that is generated may then be provided to specific components on the motorized vehicle.

One such component, the Vehicle Decision Module (VDM) 119, activates an electrical or mechanical component such as a Vehicle Interlock 117 to prevent the movement of the vehicle for any TAC measured value greater than 0 in a zero tolerance embodiment. The other component, the Driver Information Interface (DII) 122, provides a digital or LED display, viewable from the driver's seat, indicating the presence or absence of alcohol or a value for the driver's BAC. This information, which may include time, temperature, and humidity, is also recorded.

Figure 4:
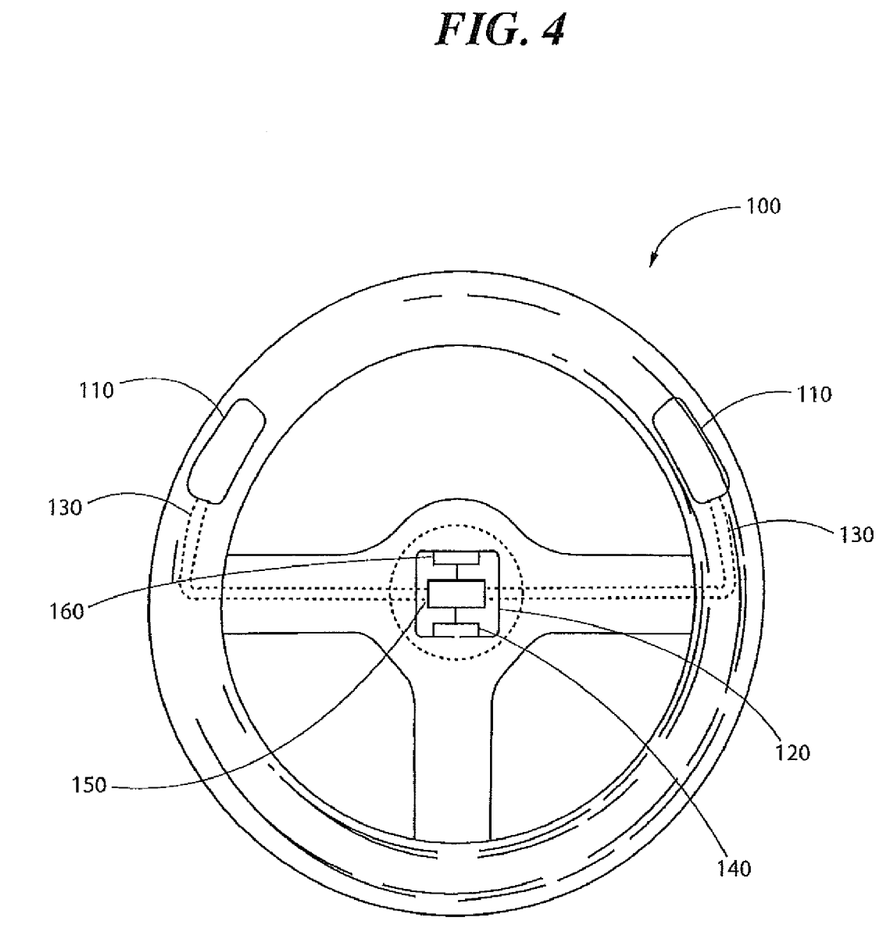
FIG. 4 is a top plan view of a steering mechanism built in accordance with the instant invention.

Referring now to FIG. 4, the components of one embodiment of the in-vehicle alcohol detection system, generally indicated as 100, are shown installed in a steering mechanism. One or more collection sites 110 are installed, preferably on the backside of the rim portion of the steering mechanism 100 in a location that facilitates the collection of pre-perspiratory vapor from the palm of the driver's hand. The collection sites 110 are mechanically connected to a sensor apparatus 120 located in the center of the steering mechanism by inert tubing 130. The sensor apparatus 120 is connected to and utilizes a low voltage (typically 12 volt) direct current power source and uses a miniature air pump 140 to draw pre-perspiratory vapor from the collection sites 110 through the inert tubing 130 to the sensor apparatus 120. Ambient temperature and humidity are also measured at the sensor apparatus 120.

Once the pre-perspiratory vapor reaches the sensor apparatus 120, it is directed to the sensor array 150 where it is exposed to the various polymers within the sensor array 150 (having a structure of sensor array 20, by way of example). As discussed above, a capacitance response pattern from a sensor is created by the interaction between the polymers on the respective n sensors 12-15 and the pre-perspiratory vapor. This capacitance response pattern 19, along with the ambient temperature and humidity measurements, is converted to a digital data signal and transmitted through an electrical connection to the computing device 160.

The computing device 160 is electronically connected to sensor apparatus 120 so that it can receive the requisite input data from the sensor array. The computing device 160 includes a processing unit in which the pattern recognition, analyte identification and interferent discrimination algorithms operate, memory for storing the pattern recognition library 116, a data storage medium, and input and output ports. Once the input is received by the pattern recognition algorithms, the artificial neural network executes, using the inputs, resulting in a TAC output. The TAC output is then transmitted, either hardwired or wirelessly, to the specified vehicle systems 117, 119, 122.

Figure 5:
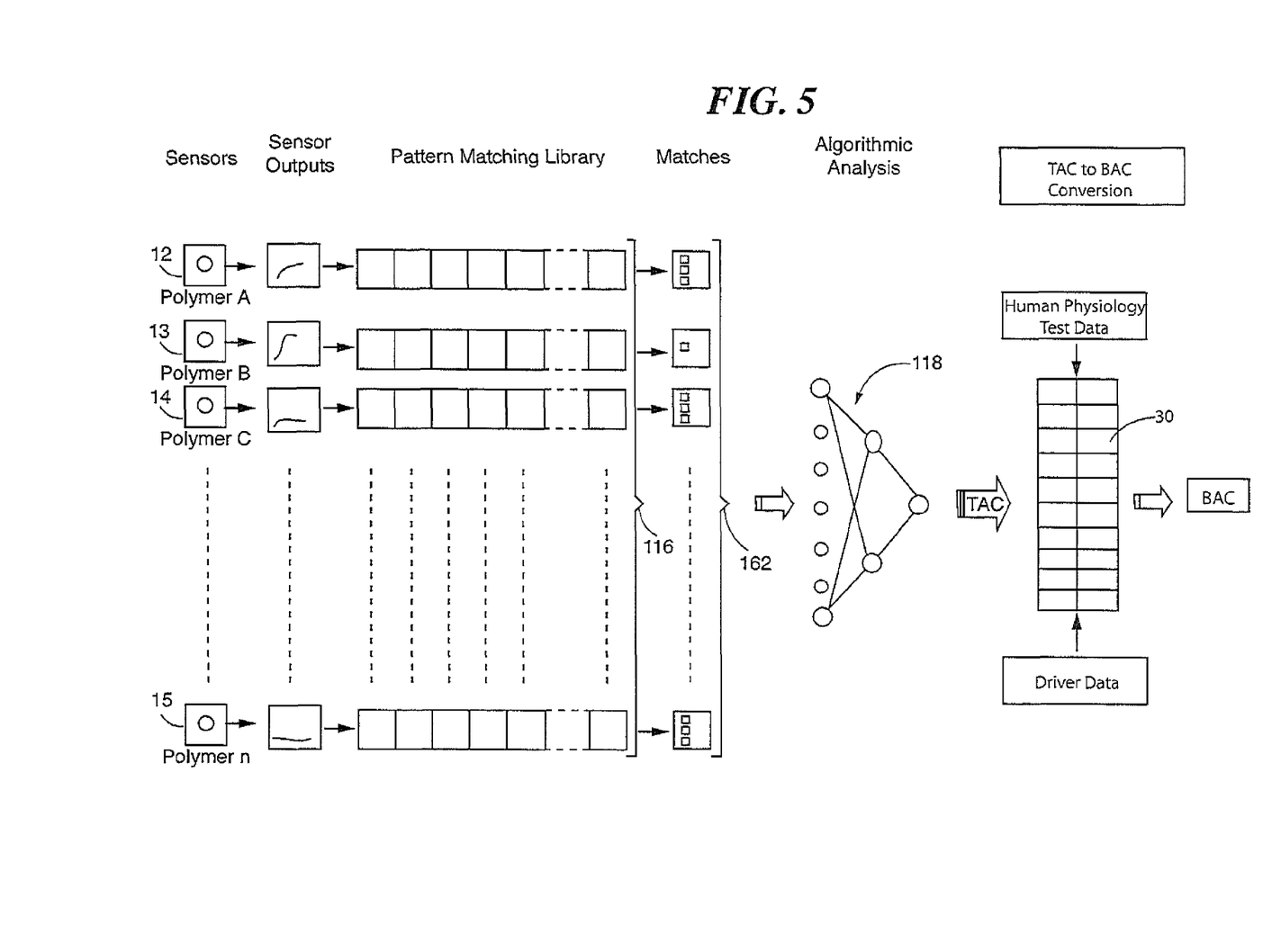
FIG. 5 is a flow chart showing the process of determining the blood alcohol concentration of a driver of a motorized vehicle and transmitting the blood alcohol concentration to systems within the motorized vehicle.

Referring now to FIG. 5, an operational diagram detailing the operation of an alternate embodiment of the in-vehicle alcohol detection system is shown. Like numerals are utilized to indicate like structure; the primary difference being the use of a database to determine BAC from TAC.

When exposed to pre-perspiratory vapor and possibly other interferents, the sensors 12-15 each produce a response signal spike 19a-19n. Taken together, these sensor response signal spikes form a sensor response pattern 19 that provides an input for the pattern recognition library 116. The computing device 160 using the output from the pattern recognition library 116, and associated pattern recognition, analyte identification and interferent discrimination algorithms, 118 to identify and quantify the analytes detected by sensor array 20 as a function of the input signal pattern. A TAC measurement is obtained through execution of the processing algorithms such as neural network 118 as discussed above.

In this embodiment, the TAC value that is generated is then input to a database, or look up table, 30 which is used by computing device 160 to convert the TAC value to its corresponding BAC value. In a preferred embodiment, the database 30 is derived form human test data and may use driver specific information as well as general empirical data, gathered through extensive human intravenous testing, to correlate the BAC of a driver with the TAC of that driver. The driver specific information may include, but is not limited to, physiological data such as gender, age, body mass index ('BMI'). In this embodiment, the BAC is provided to the Vehicle Decision Module 117 and the Driver Information Interface 122. The Vehicle Decision Module 117, in this embodiment, will cause the vehicle to be immobilized only if the driver's BAC value is above a preset limit chosen at the time the system is set up. The Driver Information Interface 122 in this embodiment provides a display (digital or LED) of the BAC value that is viewable from the driver's seat.

The above examples are provided in connection with the steering wheel for an automobile. However, this invention is applicable to the operational controls of any vehicle or machinery utilizing hand controls. By providing the sensor array and pattern matching library as discussed above, to be processed in accordance with algorithmic analysis, a control system for any operating control associated with vehicles and/or heavy machinery may be provided which prevents operation of the device in the presence of alcohol use by an operator. Furthermore, although neural networks are discussed above in connection with the algorithm analysis performed by the CPU or ASIC CHIP, other statistical models may be utilized to predict the probability that a TAC level is present as a function of sensing pre-perspiratory vapors from the operator. Lastly, chemicapacitive sensor array is used by way of example. Other sensor technologies capable of creating a unique sensor pattern in the presence of pre perspiratory vapor, such as chemi-resistive, metal oxide and electrochemical sensors may be used.

The instant invention has been shown and described herein in what is considered to be the most practical and preferred embodiment. It is recognized, however, that departures may be made therefrom within the scope of the invention and that obvious modifications will occur to a person skilled in the art. Other immediate applications, of the above described technology, include, but are not limited to, the steering or control mechanisms in planes, trains, ships, heavy equipment and nuclear reactors.

What is claimed as new and desired to be protected by Letters Patent of the United States is:

1. An apparatus for detecting and measuring ethyl alcohol in the bloodstream comprising:

an array of sensors adapted to process the pre-perspiratory vapor emanating from a person, the pre-perspiratory vapor containing one or more analytes;

each sensor in the array of sensors producing a signal in response to the analytes present; at least one sensor producing an identifiable signal to an analyte of ethanol; and at least two sensors in the sensor array producing a respective signal in response to an identical analyte, the signal output by a first of the at least two sensors having a predetermined difference from the signal output by a second of the at least two sensors;

a pattern recognition library storing signal patterns corresponding to one or more outputs of the array of sensors; and a computing device receiving individual outputs from the array of sensors, the individual outputs exhibiting a pattern, including the predetermined difference, and comparing the pattern formed by the individual outputs to the signal patterns stored in the pattern recognition library, and determining a transdermal alcohol content measurement as a function of the comparison.

2. The apparatus of claim 1 wherein the computing device determines the transdermal alcohol content measurement through neural network analysis of the outputs of the pattern recognition library.

3. The apparatus of claim 1 in which the output of the sensor s a function of change of capacitance in the presence of a target analyte.

4. The apparatus of claim 1 wherein at least one sensor in the array of sensors is a sensor for ambient humidity.

5. The apparatus of claim 4 wherein at least one sensor in the array is a sensor for ambient temperature.

6. The apparatus of claim 1 wherein the computing device determines a transdermal alcohol content by determining that a portion of the pattern formed by the individual outputs corresponds to interferents and subtracting the portion of the pattern attributable to interferents from the pattern formed by the individual outputs.

7. The apparatus of claim 1 wherein the apparatus is disposed within a vehicle, the vehicle comprising an operational control, at least the sensors being disposed in the operational control, the operational control being required to come in contact with a user of the vehicle for operation of the vehicle, and further comprising a vehicle decision module in communication with the computing device and receiving a signal from the computing device as a function of the transdermal alcohol content measurement, the vehicle decision module preventing movement of the vehicle as a function of the transdermal alcohol content measurement.

8. The system of claim 7 wherein said operational control is a steering wheel.

9. The apparatus of claim 8 wherein said pattern recognition library and computing device are disposed on said operational control.

10. The apparatus of claim 8 further comprising a driver information interface receiving the output signal from the computing device and providing a display viewable to the operator of the vehicle indicating the presence or absence of alcohol in the bloodstream of the operator.

11. The apparatus of claim 1 further comprising a human database, the human database storing conversion data for converting the transdermal alcohol content measurement to a blood alcohol content measurement, the computing device being operatively connected to the human database for determining the blood alcohol content of the person.

12. The apparatus of claim 8 further comprising a driver information interface receiving the output signal from the computing device and providing a display viewable to the operator of the vehicle indicating the presence or absence to concentration of alcohol in the bloodstream of the operator.

13. The apparatus of claim 1, wherein the computing device determines the transdermal alcohol content and measurement through statistical analysis of the outputs of the pattern recognition library.

\* \* \* \* \*